United States Patent
Woestenborghs et al.

(10) Patent No.: US 9,856,203 B2
(45) Date of Patent: Jan. 2, 2018

(54) PROCESS FOR THE ISOLATION OF LEVULINIC ACID

(71) Applicant: Georgia-Pacific LLC, Atlanta, GA (US)

(72) Inventors: Pierre Louis Woestenborghs, Echt (NL); Rinke Marcel, Echt (NL)

(73) Assignee: Georgia-Pacific LLC, Atlanta, GA (US)

( * ) Notice: Subject to any disclaimer, the term of this patent is extended or adjusted under 35 U.S.C. 154(b) by 0 days.

(21) Appl. No.: 14/904,775

(22) PCT Filed: Jul. 10, 2014

(86) PCT No.: PCT/EP2014/064796
§ 371 (c)(1),
(2) Date: Jan. 13, 2016

(87) PCT Pub. No.: WO2015/007602
PCT Pub. Date: Jan. 22, 2015

(65) Prior Publication Data
US 2016/0168067 A1    Jun. 16, 2016

(30) Foreign Application Priority Data
Jul. 17, 2013  (EP) .................................... 13176808

(51) Int. Cl.
| | | |
|---|---|---|
| C07C 51/48 | (2006.01) |
| C07C 51/44 | (2006.01) |
| D21C 11/00 | (2006.01) |
| C09K 3/00 | (2006.01) |

(52) U.S. Cl.
CPC .............. *C07C 51/48* (2013.01); *C07C 51/44* (2013.01); *C09K 3/00* (2013.01); *D21C 11/0007* (2013.01)

(58) Field of Classification Search
CPC ....... C07C 51/48; C07C 59/185; C07C 51/44; C09K 3/00; D21C 11/0007

USPC ........................................... 252/364; 562/577
See application file for complete search history.

(56) References Cited

U.S. PATENT DOCUMENTS

| | | | |
|---|---|---|---|
| 6,054,611 A | 4/2000 | Farone et al. | |
| 2010/0312006 A1 | 12/2010 | Lake et al. | |
| 2014/0128634 A1* | 5/2014 | Mullen | C07C 51/00 562/577 |

FOREIGN PATENT DOCUMENTS

| | | |
|---|---|---|
| CN | 105209421 A | 12/2015 |
| WO | 2013/078391 A1 | 5/2013 |
| WO | 2014/159992 A1 | 10/2014 |

OTHER PUBLICATIONS

Dow ("Physical Properties | Caustic Soda | The Dow Chemical Company", p. 1, downloaded from http://www.dow.com/causticsoda/offer/physical.htm on Sep. 29, 2016).*
Slagt ("Ion Exchange Resin Selection" p. 1-38, downloaded from http://www.soci.org/~/media/Files/Conference%20Downloads/2012/IEX%20Intro%20Water%20Sept%202012/Marc_Slagt_resin.ashx on Sep. 30, 2016).*
International Search Report from corresponding PCT/EP2014/064796, dated Sep. 16, 2014.

* cited by examiner

*Primary Examiner* — Rosalynd A Keys
*Assistant Examiner* — Amy C Bonaparte
(74) *Attorney, Agent, or Firm* — Ram W. Sabnis

(57) ABSTRACT

The invention relates to a process for the isolation of levulinic acid from an organic solution, comprising washing said organic solution with an alkaline aqueous stream to yield a washed organic solution; subjecting the washed organic solution to a distillation to yield a distillate and a distillation residue; and recovering levulinic acid from the distillate or the residue. This process may result in high yields of levulinic acid.

11 Claims, No Drawings

PROCESS FOR THE ISOLATION OF LEVULINIC ACID

CROSS REFERENCE TO RELATED APPLICATIONS

This application is a §371 National Stage Application of PCT/EP2014/064796, filed 10 Jul. 2014 which claims priority to EP13176808.7, filed 17 Jul. 2013.

BACKGROUND

Field of the Invention

This invention relates to a process for the isolation of levulinic acid from an organic solution, to the use of an alkaline aqueous stream in the isolation of levulinic acid, and to a process for the production of levulinic acid from a lignocellulosic biomass.

Description of Related Art

Levulinic acid is a starting molecule for the synthesis of esters known as fuel additive and is known to be useful as plasticiser and solvent. Levulinic acid can be used to synthesize methyl tetrahydrofuran (MTHF) or can be used as a solvent. Other applications of levulinic acid are for example the synthesis of delta-amino levulinic acid used as herbicides and pesticides, diphenolic acid used to synthesize polycarbonates and succinic acid used to make polyesters. Levulinic acid can also be used to produce gamma valerolactone (5-methylbutyrolactone), which in turn can be used for production of adipic acid (1,6-hexanedioic acid).

Levulinic acid may be produced by acid hydrolysis of biomass, as is described for example in U.S. Pat. Nos. 5,608,105, 4,897,497, and 6,054,611. After the acid hydrolysis reaction the levulinic acid must be purified from unwanted components and side products. US2010312006 suggests using solvent-extraction to isolate levulinic acid from a biomass hydrolysate, and suggests including a distillation step after solvent extraction to further purify the separated levulinic acid.

SUMMARY

In one aspect the invention provides a process for the isolation of levulinic acid from an organic solution, comprising:
  washing said organic solution with an alkaline aqueous stream to yield a washed organic solution;
  subjecting the washed organic solution to a distillation to yield a distillate and a distillation residue; and
  recovering levulinic acid from the distillate and/or the residue.

DETAILED DESCRIPTION OF A PREFERRED EMBODIMENT

The inventors have found that the yield of levulinic acid is insufficient when a levulinic acid containing stream is first subjected to solvent-extraction and subsequently to distillation. They have surprisingly found that the yield can be improved when the organic solution, prior to distillation, is washed with an alkaline aqueous stream.

In the context of the invention, "alkaline aqueous stream" is understood to be an aqueous liquid of alkaline pH.

The alkaline aqueous stream may also be a solution containing e.g. salts and/or trace elements. Using an alkaline aqueous stream to wash the organic solution may advantageously result in a greater purity of the levulinic acid in the distillate as compared to having no washing, or washing with an aqueous, non-alkaline stream.

The organic solution comprises levulinic acid and preferably also formic acid and/or acetic acid. The organic solution is preferably a clear solution, that is, its components are preferably dissolved, and the solution is preferably immiscible with water. The amount of levulinic acid in the organic solution is not critical, and can range between 0.1 and 10 wt %, preferably between 1 and 5 wt %, more preferably between 2 and 4 wt %. If the organic solution comprises formic acid, its concentration is preferably between 0.1 and 10 wt %, more preferably between 0.2 and 5 wt %, more preferably between 0.5 and 2 wt %. If the organic solution comprises acetic acid, its concentration is preferably between 0.001 and 0.5 wt %, more preferably between 0.005 and 0.1 wt %, more preferably between 0.01 and 0.05 wt %.

The solvent of the organic solution preferably comprises MTHF. For example, the organic solution may be MTHF comprising dissolved levulinic acid.

The washing step results in a washed organic solution and a spent washing aqueous stream. For the sake of convenience, in this specification said spent washing aqueous stream will be referred to as "spent washing water".

After washing the organic solution with the alkaline aqueous stream at least part of the levulinic acid will end up in the resulting washed organic solution. Preferably at least 50 wt % of the levulinic acid in the organic solution remains in the washed organic solution, more preferably at least 60%, 70%, even more preferably at least 80%, 90%, even more preferably at least 95%, 99% of the levulinic acid initially present in the organic solution ends up in the washed organic solution. The amount of alkaline aqueous stream to wash the organic solution is not critical, but is typical 0.5-2 times the volume of the organic solution. However, smaller or greater volumes are also possible.

The process may include multiple washing steps with the alkaline aqueous stream. This may improve the distillation efficiency even more. For example, the organic solution may be washed by a first alkaline aqueous stream, resulting in a first washed organic solution. Then, the first washed organic solution may be washed again with the first alkaline aqueous stream, or preferably with a second alkaline aqueous stream, resulting in a second washed organic solution. This process may be repeated.

Alternatively, the organic solution may be washed with one or more non-alkaline aqueous streams or one or more alkaline aqueous streams. For example, the organic solution may be washed with a non-alkaline aqueous stream (e.g. water) and subsequently with an alkaline aqueous stream. Alternatively, the organic solution may be washed with an alkaline aqueous stream and subsequently with a non-alkaline aqueous stream (e.g. water).

The alkaline aqueous stream may comprise a base. The alkaline aqueous stream may comprise additional components such as salts.

In an embodiment the base comprises an inorganic base, such as NaOH, KOH, $NH_3$, sodium (bi) carbonate, or a mixture thereof. The concentration of the base is not critical, and is typically around 1% (w/v).

In another embodiment the base is an organic base, such as organic amine.

In yet another embodiment the alkaline aqueous stream comprises a liquor stream from a paper plant. For example, a liquor stream from a paper plant, which otherwise would be discarded, can be used to wash the organic solution. After the washing step, the spent washing water resulting from this can be fed back to the paper plant, for example to a so-called "black liquor burner". Since a liquor stream from a paper plant may already be alkaline, adding base may not be required. Also, because said liquor stream is an aqueous stream, the consumption of water in the process of the invention may be less.

Preferably, the alkaline aqueous stream has a pH between 8 and 14, more preferably a pH between 9 and 14, even more preferably between 10 and 14. If the pH is too low, e.g. less than 8, the improvement in the distillation step may be less. The upper pH value is less critical. However, for reason of economics, the mount of base is preferably not greater than needed for optimal effect. The skilled person can easily, without burden, test and determine the optimal amount of base required to arrive at a suitable pH.

The levulinic acid may be recovered as a distillate and/or as a distillation residue. Preferably the levulinic acid is recovered as a distillate. In the context of the invention, the term "a distillation" does not necessarily mean that there is only one distillation. The process may comprise a single distillation step (or unit). Alternatively, the process may comprise one, two, or more distillation units. If the process comprises more than one distillation unit, levulinic acid is preferably recovered as a distillate of at least one distillation unit. Levulinic acid may be recovered as a distillate of two or more distillation units. If there are more distillation units, levulinic acid is preferably recovered as a distillate of the final distillation unit, but may also be recovered as a distillate or residue of an intermediate distillation unit. For example, a first distillation may be done with the purpose to remove the solvent; levulinic acid can be recovered as the distillation residue. This residue can be subjected to a second distillation, from which levulinic acid can be isolated as a distillate. Alternatively, this second distillation can be done with the purpose to remove any lights such as formic acid or acetic acid, in which case levulinic acid can be recovered as a distillation residue, which residue can then be subjected to a third distillation, from which levulinic acid can be recovered as a distillate. Thus, depending on the composition of the washed organic solution, the skilled person can devise a distillation scheme such that in levulinic acid is suitably recovered.

In an embodiment, particularly if the solvent comprises MTHF, water may be added to the distillation. This may advantageously allow for cost-efficient recovery and recycling of MTHF. Water can be added to the distillation together with (as part of) the washed organic solution; for example, water can be added to the washed organic solution prior to feeding said solution to the distillation. However, care must be taken that adding water to the washed organic solution does not result in the formation of a biphasic solution. It is important that the washed organic solution is a monophasic solution prior to distillation. If it is preferred that water is to be added as part of the washed organic solution, the skilled person can simply perform a lab or pilot experiment in order to determine the maximal amount of water that can be added to the washed organic solution such that the washed organic solution still assumes a monophasic solution.

Alternatively, water can be added to the distillation separately from the washed organic solution, that is, the water and the washed organic solution can be added to the distillation separately. Preferably water is added at the top of the distillation, even more preferably by reflux.

In an embodiment, the process comprises the step of solvent-extraction, resulting in an organic solution comprising levulinic acid, and an aqueous solution, and recovering said organic solution. The recovered organic solution may be washed by an alkaline aqueous stream according to the process of the invention to yield a washed organic solution.

In an embodiment the process comprises subjecting a (preferably aqueous) composition comprising levulinic acid and optionally comprising formic acid and/or acetic acid to solvent-extraction, preferably by adding a solvent, to yield an organic solution comprising levulinic acid and optionally formic acid and/or acetic acid, and recovering the organic solution. The recovered organic solution can be washed with the alkaline aqueous stream according to the process of the invention.

The extraction can be carried out such that a solvent is added to the composition comprising levulinic acid optionally formic acid and/or acetic acid in a suitable amount, resulting in a biphasic system. The resulting phases can be separated, e.g. by decantation, resulting in an organic solution, to be washed with the alkaline aqueous stream, and an aqueous solution. The skilled person knows how to separate the two layers.

In the context of the invention, "extraction", "solvent extraction", and "solvent-solvent extraction" are understood to be the same. Extraction takes advantage of differences in the chemical properties of the feed components, such as differences in polarity and hydrophobic/hydrophilic character to separate them (T. C. Frank, L. Dahuron, B. S. Holden, W. D. Prince, A. F. Seibert, L. C. Wilson, Liquid-liquid extraction and other liquid-liquid operations and equipment in Perry's Chemical Engineering Handbook, 8th Edition, Section 15). Extraction yields an aqueous solution, also referred to as aqueous phase, and an organic solution, also referred to as organic phase. A preferred organic solvent is methyl tetrahydrofuran (MTHF). The aqueous solution may comprise mineral acid and/or salts.

The composition comprising levulinic acid and optionally comprising formic acid and/or acetic acid may comprise additional components, preferably formic acid.

The composition comprising levulinic acid and optionally comprising formic acid and/or acetic acid is preferably a biomass hydrolysate. Such biomass hydrolysate is obtained by (preferably acid) hydrolysis under conditions such that it results in the formation of levulinic acid. Suitable acids for acid hydrolysis of biomass include sulphuric acid, hydrochloric acid, and phosphoric acid. A preferred acid is sulphuric acid, preferably diluted sulphuric acid, for example at a concentration between 1.5-10%. The temperature in the acid hydrolysis may depend on the source of carbohydrates, and may range between 150-250° C., preferably between 170-240° C., more preferably between 190-230° C., even more preferably between 200 and 220° C. The acid hydrolysis may comprise one, two, or more stages. The pressure may also depend on the source of carbohydrates, as well as on the temperature, and may be anywhere between 1 and 50 bar, preferably between 5 and 40 bar, even more preferably between 10 and 30 bar. Suitable reactors include plugflow reactors, backmix reactors, and CSTR reactors. Different reactors for different stages may be used.

The biomass to be hydrolyzed may be or may be derived from wood, grass, cereal, starch, algae, tree bark, hay, straw, leaves, paper pulp, paper sludge, or dung. Paper pulp, or simply pulp, is a lignocellulosic fibrous material prepared by chemically or mechanically separating cellulose from wood, fibre crops or waste paper. Pulp is rich in cellulose and other carbohydrates. Paper sludge, or simply sludge, is a lignocellulosic fibrous containing cellulose fibres too short for usage in the paper industry.

The biomass preferably comprises lignocellulosic biomass. Lignocellulosic biomass typically has a fibrous nature and comprises a bran fraction that contains the majority of lignocellulosic (bran) fibers. As an example, corn fiber is a heterogeneous complex of carbohydrate polymers and lignin. It is primarily composed of the outer kernel covering or seed pericarp, along with 10-25% adherent starch. Carbohydrate analyses of corn fiber vary considerably according to the source of the material. The lignocellulosic biomass may comprise hemicellulose. A preferred biomass is paper pulp or paper sludge.

In one embodiment, extraction of levulinic acid from a biomass hydrolysate, preferably using MTHF as solvent, is done in a first column resulting in an organic solution comprising levulinic acid, and an aqueous solution. The organic solution comprising levulinic acid is washed with an alkaline aqueous stream in a second column to yield spent washing water and a washed organic solution comprising levulinic acid. The spent washing water is discarded.

In another embodiment, extraction of levulinic acid from a biomass hydrolysate, preferably using MTHF as solvent, is done in a first column resulting in an organic solution comprising levulinic acid, and an aqueous solution. The organic solution comprising levulinic acid is washed with an alkaline aqueous stream in a second column resulting in spent washing water, and a washed organic solution comprising levulinic acid. The spent washing water is fed (back) to the extraction column, together with (fresh) biomass hydrolysate. This may have the advantage that more levulinic acid may be recovered from the spent washing water, or less may be lost.

In yet another embodiment, both extraction of levulinic acid from of a biomass hydrolysate, preferably with MTHF, and washing of the organic solution comprising levulinic acid with an alkaline aqueous stream are done in the same column. An alkaline aqueous stream is fed to the column above the point where a biomass hydrolysate is fed, preferably the alkaline aqueous stream is fed at the top of the column and the biomass hydrolysate is fed at below this point. The exact positions of the feed into the column are not critical, and can easily be calculated by a person skilled in the art. This embodiment has the same advantages and disadvantages as the previous embodiment, and has the additional advantage that only one column is required.

In an embodiment the process of the invention comprises:
 subjecting a slurried lignocellulosic biomass to an acid hydrolysis reaction in the presence of a mineral acid and under conditions of temperature, time, and acid concentration to yield a biomass hydrolysate comprising levulinic acid;
 subjecting the biomass hydrolysate to a solvent-extraction, preferably by adding an organic solvent, to yield an aqueous solution and an organic solution comprising levulinic acid, and recovering said organic solution.

In another aspect the invention provides a process for the production of levulinic acid from a lignocellulosic biomass comprising:
 subjecting a slurried lignocellulosic biomass to an acid hydrolysis reaction in the presence of a mineral acid and under conditions of temperature, time, and acid concentration to yield a biomass hydrolysate comprising levulinic acid;
 subjecting the biomass hydrolysate to a solvent-extraction, preferably by adding an organic solvent, preferably MTHF to the biomass hydrolysate to yield an aqueous solution (or aqueous phase), and an organic solution (or organic phase) comprising levulinic acid, and recovering said organic solution (or organic phase);
 washing said organic solution (or organic phase) comprising levulinic acid with an alkaline aqueous stream to yield a washed organic solution comprising levulinic acid;
 subjecting the washed organic solution comprising levulinic acid to a distillation to yield a distillate and a distillation residue; and
 recovering levulinic acid from the distillate and/or the residue.

In a further aspect the invention provides the use of an alkaline aqueous stream to improve the isolation of levulinic acid from an organic solution.

EXAMPLES

Example 1

In a tantalum-lined autoclave 1 L of a biomass slurry, consisting of 10 wt % bleached paper pulp in water, was heated to 175° C. Upon reaching this temperature sulfuric acid was injected until a sulfuric acid concentration of 4 wt %. The mixture was stirred for 75 minutes, next the reactor content was discharged and cooled to room temperature within a few minutes. The solids were filtered off, resulting in a liquid biomass hydrolysate, containing approximately 4 wt % levulinic acid. To obtain the necessary volumes for the extraction several batches were united and mixed to yield 1500 gram of liquid biomass hydrolysate. This liquid biomass hydrolysate was concentrated to 733 g under reduced pressure at 60° C. under stirring. Next, 200 mL of MTHF was added, the mixture was stirred for 30 min, and the phases were separated. The organic phase was collected. This procedure was repeated in total 5 times with 200 mL MTHF in each extraction. The organic phases (total 1071 g) were combined and the aqueous phase was discarded. The combined organic phase was shown to contain 3 wt % levulinic acid, 0.77 wt % formic acid, and 0.027 wt % acetic acid. The combined organic phase was heated under stirring until 60° C., next a 1 wt % aqueous NaOH solution (100 g) was added (0.25 M, pH 13.4). The mixture was stirred for 30 min and the phases were separated, resulting in an aqueous NaOH solution (103 g), which was discarded, and an organic phase (1063 g), which was recovered. To 971 g of this organic phase was added 50 g water. The mixture was subjected to a first distillation in order to remove the MTHF, at atmospheric pressure until the bottom temperature was 100° C. The top product was discarded and the bottom product (137 g) was collected. The results of the first distillation are stated in Table 1.

TABLE 1

Concentrations of first distillation

| | MTHF wt % | Formic acid wt % | Acetic acid wt % | Levulinic acid wt % | Water (wt %) | total mass of fraction (g) |
|---|---|---|---|---|---|---|
| starting material | 89.3 | 0.77 | 0.02 | 3.0 | 6.85 | 10 |
| bottom product | 0.25 | 5.3 | 0.14 | 21.3 | 70 | 13 |
| product balance | | 97.1 | 98.8 | 100 | | |

The bottom product of the first distillation (133 g of the 137 gram) was subjected to a second distillation, in order to remove any lights, using a 50 cm Vigreux column at 100 mbar. The pressure was kept constant and the temperature was steadily increased until an oil bath temperature of 130° C. The temperature profile is given in Table 2

TABLE 2

Temperature profile of the first distillation

| $T_{oil\ bath}$ | $T_{bottom}$ | $T_{top}$ |
|---|---|---|
| 75 | 40 | 22 |
| 85 | 42 | 40 |
| 100 | 46 | 42 |
| 130 | 115 | no vapor condensation |

Two top fraction and one bottom product was collected. The product that was collected in the cold trap of the vacuum pump was also analyzed. The distillation was stopped when the oil bath temperature reached 130° C. and no vapors reached the top of the distillation. The results of the second distillation are stated in Table 3.

TABLE 3

Concentrations of the second distillation

| | MTHF | Formic acid | Acetic acid | Levulinic acid | total mass of fraction |
|---|---|---|---|---|---|
| starting material | 0.25 wt % | 5.3 wt % | 0.14 wt % | 21.3 wt % | 133 g |
| top fraction I | | 2.2 wt % | 0.14 wt % | 325 ppm | 36.6 g |
| top fraction II | | 9.6 wt % | 0.48 wt % | 160 ppm | 35.2 g |
| bottom product | | 1.5 wt % | | 83.3 wt % | 33.5 g |
| cold trap fraction | | 0.34 wt % | 0.34 wt % | 600 ppm | 25.5 g |
| product balance | | 89.9% | | 98.5% | 98.0% |

The bottom product of the second distillation (33 g of the 33.5 g) was subjected to a third distillation using a 50 cm Vigreux column at a constant pressure of 5 mbar and an oil bath temperature starting at 185° C. The temperature profile is given in Table 4.

TABLE 4

Temperature profile of the third distillation

| $T_{oil\ bath}$ | $T_{bottom}$ | $T_{top}$ |
|---|---|---|
| 185 | 136 | 113 |
| 185 | 140 | 118 |
| 185 | 140 | 118 |
| 195 | 143 | 118 |

To determine the levulinic acid that remained in the column the column was washed with acetone after the distillation was finished. The wash liquid was weight to be 71 g and its levulinic acid concentration was determined. The results of the distillation are in Table 5. Levulinic acid could be isolated with this method to a purity of 96.9 wt %. With a continuous distillation at bigger scale, even higher purities may be achieved.

TABLE 5

Concentrations of the third distillation

| | Formic acid | Levulinic acid | total mass fraction | total mass levulinic acid |
|---|---|---|---|---|
| starting material | 1.5 wt % | 83.3 wt % | 33.0 g | 27.5 g |
| top fraction I | | 88.3 wt % | 3.0 g | 2.6 g |
| top fraction II | 96.9 wt % | 17.0 g | 16.5 g | |
| bottom product | 51.8 wt % | 10.1 g | 5.2 g | |
| remainder in column | 3.6 wt % | 2.6 g | 2.6 g | |
| product balance | 97.9% | 98.9% | 26.9 g | |

Comparative Example A

A liquid biomass hydrolysate (1500 grams) was made according to Example 1, and was concentrated to half of its weight under reduced pressure at 60° C. The concentrated, liquid biomass hydrolysate was heated under stirring until 60° C., next 200 mL MTHF was added. The mixture was stirred for 30 min, the phases were separated, and the organic phase was collected. This procedure was repeated in total 5 times, with 200 mL MTHF in each extraction. The organic phases were combined. The aqueous phase was discarded. The combined organic phase (1000 g) was shown to contain 3.3 wt % levulinic acid, 0.9 wt % formic acid, and 0.026 wt % acetic acid. The combined organic phase was heated under stirring until 60° C.; next 100 grams of water was added. The resulting mixture was stirred for 30 min and the phases were separated. The organic phase was recovered and the aqueous phase was discarded. To recovered organic phase, 30 g water was added. The mixture was subjected to a first distillation to remove the MTHF at atmospheric pressure until the bottom temperature was 100° C. The top product was discarded and the bottom product (98 g) was recovered. The results of the first distillation are stated in Table 6.

The recovered bottom product of the first distillation (98 g) was subjected to a second distillation using a 50 cm Vigreux column at 100 mbar, to remove the lights. The pressure was kept constant and the temperature was steadily increased until 130° C. The temperature profile is given in Table 7.

TABLE 6

Concentration of the first distillation

|  | MTHF | Formic acid | Acetic acid | Levulinic acid | water | total mass of fraction |
|---|---|---|---|---|---|---|
| starting material |  | 0.9 wt % | 0.026 wt % | 3.3 wt % |  | 841 g |
| bottom product | 0.37 wt % | 7.5 wt % | 0.21 wt % | 28.5 wt % | 58.6 wt % | 98 g |
| product balance |  | 97.1% | 94.1% | 100% |  |  |

Two top fractions and one bottom fraction were collected. The product collected in the cold trap of the vacuum pump was also analyzed. The distillation was stopped when the oil bath temperature reached 130° C. and no vapors reached the top of the distillation.

TABLE 7

Temperature profile of the second distillation

| $T_{oil\ bath}$ | $T_{bottom}$ | $T_{top}$ |
|---|---|---|
| 75 | 40 | 22 |
| 85 | 42 | 40 |
| 100 | 46 | 42 |
| 130 | 120 | no vapor condensation |

The results of the second distillation are shown in Table 8. The amount of formic acid missing to close the mass balance will be found in the cold trap which was not analyzed for its chemical content.
The bottom product of the second distillation (34.5 g) was subjected to a third distillation using a 50 cm Vigreux column at a constant pressure of 5 mbar and an oil bath temperature starting at 185° C. The temperature profile is given in Table 9.
To determine the levulinic acid that remained in the column, the column was washed with acetone after the distillation was finished. The wash liquid was weight to be 73.4 g and its levulinic acid concentration was determined. The results of the distillation are in Table 10. Levulinic acid could be isolated with this method in a maximum purity of only 87.1 wt %. The mass balance of levulinic acid is only 78.2% which means that 6.2 g of the starting 27.5 g levulinic acid could not be isolated in the product using this method.

TABLE 8

Concentrations of the second distillation.

|  | MTHF | Formic acid | Acetic acid | Levulinic acid | total mass of fraction |
|---|---|---|---|---|---|
| starting material | 0.37 wt % | 7.5 wt % | 0.21 wt % | 28.5 wt % | 98 g |
| top fraction I |  | 4.25 wt % | 0.21 wt % | 550 ppm | 43.1 g |
| top fraction II |  | 12.7 wt % | 0.75 wt % | 1970 ppm | 13.1 g |
| bottom product |  | 3.9 wt % |  | 78.8 wt % | 35.5 g |
| cold trap fraction |  |  |  |  | 2.0 g |
| product balance |  | 48.3% |  | 100% | 97.1% |

TABLE 9

Temperature profile of the third distillation

| $T_{oil\ bath}$ | $T_{bottom}$ | $T_{top}$ |
|---|---|---|
| 185 | 136 | 113 |
| 185 | 140 | 118 |
| 185 | 140 | 118 |
| 195 | 143 | 118 |

TABLE 10

Concentrations of the third distillation.

|  | Formic acid | Levulinic acid | total mass fraction | total mass levulinic acid |
|---|---|---|---|---|
| starting material | 3.9 wt % | 78.8 wt % | 35.5 g | 27.5 g |
| top fraction I |  | 60.5 wt % | 5.7 g | 3.4 g |
| top fraction II |  | 87.1 wt % | 12.7 g | 11.1 g |
| bottom product |  | 44.4 wt % | 9.1 g | 4.0 g |
| remainder in column |  | 3.7 wt % | 2.7 g | 2.7 g |
| fraction in cold trap | 46.1 wt % | 0.4 wt % | 4.2 g | 0.3 g |
| product balance |  | 78.2% | 99.7% | 21.3 g |

The invention claimed is:
1. A process for the production of levulinic acid from a lignocellulosic biomass, comprising:
subjecting a slurried lignocellulosic biomass to an acid hydrolysis reaction in the presence of a mineral acid at a temperature between 170° C. and 240° C. and under conditions of time and acid concentration to yield a biomass hydrolysate comprising levulinic acid;
subjecting the biomass hydrolysate to an extraction with an organic solvent to yield an aqueous solution and an organic solution, and recovering said organic solution;
washing said organic solution with an alkaline aqueous stream comprising a liquor stream from a paper plant to yield a washed organic solution;
subjecting the washed organic solution to a distillation to yield a distillate and a distillation residue; and recovering levulinic acid from at least one of the distillate and the residue.

2. The process according to claim 1, wherein the slurried lignocellulosic biomass comprises less than 10 wt % of the mineral acid.

3. The process according to claim 1, wherein the slurried lignocellulosic biomass comprises less than 10 wt % of the mineral acid, and wherein the organic solvent comprises methyl tetrahydrofuran.

4. The process according to claim 1, wherein the slurried lignocellulosic biomass comprises greater than 1.5 wt % to less than 10 wt % of the mineral acid, and wherein the organic solvent comprises methyl tetrahydrofuran.

5. The process according to claim 1, wherein the alkaline aqueous stream has a pH of 8 to 14.

6. The process according to claim 1, wherein the alkaline aqueous stream further comprises an inorganic base.

7. The process according to claim 1, wherein the alkaline aqueous stream further comprises sodium hydroxide, potassium hydroxide, ammonia, sodium bicarbonate, or a mixture thereof.

8. The process according to claim 1, wherein the alkaline aqueous steam further comprises an organic amine.

9. The process according to claim 1, wherein the slurried lignocellulosic biomass is subjected to the acid hydrolysis reaction in the presence of the mineral acid at a temperature between 190° C. and 240° C.

10. The process according to claim 1, wherein the slurried lignocellulosic biomass is subjected to the acid hydrolysis reaction in the presence of the mineral acid at a temperature between 200° C. and 240° C.

11. The process according to claim 1, wherein at least 50 wt % of the levulinic acid in the organic solution remains in the washed organic solution.

* * * * *